United States Patent
Snyder

(10) Patent No.: US 9,546,208 B2
(45) Date of Patent: Jan. 17, 2017

(54) REMOVAL OF IMPURITIES FROM PROTEIN A ELUATES

(71) Applicant: Bio-Rad Laboratories, Inc., Hercules, CA (US)

(72) Inventor: Mark Snyder, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 129 days.

(21) Appl. No.: 14/589,633

(22) Filed: Jan. 5, 2015

(65) Prior Publication Data

US 2015/0191529 A1 Jul. 9, 2015

Related U.S. Application Data

(60) Provisional application No. 61/923,380, filed on Jan. 3, 2014.

(51) Int. Cl.
| | | |
|---|---|---|
| *C07K 1/32* | (2006.01) | |
| *C07K 1/14* | (2006.01) | |
| *C07K 16/00* | (2006.01) | |
| *C07K 14/31* | (2006.01) | |
| *A61K 38/00* | (2006.01) | |

(52) U.S. Cl.
CPC ............... *C07K 16/00* (2013.01); *C07K 14/31* (2013.01); *C07K 2317/10* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,151,504 | A | 9/1992 | Croze |
| 6,127,526 | A | 10/2000 | Blank |
| 6,333,398 | B1 | 12/2001 | Blank |
| 6,797,814 | B2 | 9/2004 | Blank |
| 6,870,034 | B2 | 3/2005 | Breece et al. |
| 7,332,289 | B2 | 2/2008 | Takeda et al. |
| 8,137,561 | B2 | 3/2012 | Kozlov et al. |
| 8,263,750 | B2 | 9/2012 | Shukla et al. |
| 8,435,406 | B2 | 5/2013 | Kozlov et al. |
| 2002/0032317 | A1 | 3/2002 | Blank |
| 2003/0201230 | A1 | 10/2003 | Kopf |
| 2004/0106180 | A1 | 6/2004 | Blank |
| 2004/0138424 | A1 | 7/2004 | Takeda et al. |
| 2004/0198957 | A1 | 10/2004 | Way et al. |
| 2005/0215769 | A1 | 9/2005 | Breece et al. |
| 2005/0272917 | A1 | 12/2005 | Jiao et al. |
| 2006/0142549 | A1 | 6/2006 | Takeda et al. |
| 2007/0219358 | A1 | 9/2007 | Zhou |
| 2008/0113421 | A1 | 5/2008 | Shaw et al. |
| 2008/0132688 | A1 | 6/2008 | Zhou |
| 2009/0050566 | A1 | 2/2009 | Kozlov et al. |
| 2009/0306351 | A1 | 12/2009 | Shukla et al. |
| 2010/0130727 | A1 | 5/2010 | Zhou |
| 2010/0172894 | A1 | 7/2010 | Brown et al. |
| 2010/0200507 | A1 | 8/2010 | Kozlov et al. |
| 2010/0234577 | A1 | 9/2010 | Mazzola et al. |
| 2011/0284446 | A1 | 11/2011 | Kozlov et al. |
| 2011/0288277 | A1 | 11/2011 | Kozlov et al. |
| 2012/0121819 | A1 | 5/2012 | Kozlov et al. |
| 2012/0122759 | A1 | 5/2012 | Brown et al. |
| 2012/0184711 | A1* | 7/2012 | Sato ............ C07K 14/31 530/324 |
| 2012/0193278 | A1 | 8/2012 | Kozlov et al. |
| 2012/0283416 | A1 | 11/2012 | Frauenschuh et al. |
| 2013/0053548 | A1 | 2/2013 | Shenoy et al. |
| 2013/0096276 | A1 | 4/2013 | Yoshida et al. |
| 2013/0171183 | A1 | 7/2013 | Schneewind |
| 2013/0197200 | A1 | 8/2013 | Bian et al. |
| 2013/0317172 | A1 | 11/2013 | Koguma et al. |

FOREIGN PATENT DOCUMENTS

| | | |
|---|---|---|
| EP | 01380589 A1 | 1/2004 |
| EP | 00950067 B1 | 8/2007 |
| EP | 01472275 B1 | 12/2008 |
| EP | 02027921 A2 | 2/2009 |
| EP | 01864999 B1 | 3/2009 |
| EP | 01897890 B1 | 11/2009 |
| EP | 02319622 A2 | 5/2011 |
| EP | 02048154 B1 | 8/2012 |
| EP | 02574618 A1 | 4/2013 |
| WO | 98/01560 A1 | 1/1998 |
| WO | 03/018596 A2 | 3/2003 |
| WO | 2009/017491 A1 | 2/2009 |
| WO | 2010/056550 A1 | 5/2010 |
| WO | 2012/164046 A1 | 12/2012 |
| WO | 2013/028330 A2 | 2/2013 |

(Continued)

OTHER PUBLICATIONS

The International Search Report and Written Opinion from International Application No. PCT/US2015/010172, dated May 29, 2015.
Balasundaram et al., "Study of the conditions for multi-modal chromatographic capture of Fab from dual-salt precipitated *E. coli* homogenate," *J. Chem. Tech. Biotech.* 88(3):372-377 (Mar. 2013).
Giovannoni et al, "Antibody Purification using membrane adsorbers," *BioPharm International*, 21(12):48-52 (Dec. 2008).
Grodzki et al., "Antibody purification: affinity chromatography—protein A and Protein G Sepharose," *Methods Mol. Biol.*, 588:34-41 (2010).
Hogwood et al., "The dynamics of the CHO host cell protein profile during clarification and protein A capture in a platform antibody purification process," *Biotechnol. Bioeng.*, 110(1):240-251 (Jan. 2013).

(Continued)

*Primary Examiner* — Anand Desai
*Assistant Examiner* — Samuel Liu
(74) *Attorney, Agent, or Firm* — Kilpatrick Townsend & Stockton LLP

(57) ABSTRACT

Modified Protein A, Protein G, Protein L, or Protein A/G that lacks antibody binding activity, and methods of the modified protein's use for purifying antibodies is provided.

17 Claims, No Drawings

(56) References Cited

FOREIGN PATENT DOCUMENTS

WO   2013/066707 A1   5/2013
WO   2013/089477 A1   6/2013

OTHER PUBLICATIONS

Kang et al. "Development of an alternative monoclonal antibody polishing step," *BioPharm. Int.*, 25(5):34-47 (2012).

Ma et al., "Using precipitation by polyamines as an alternative to chromatographic separation in antibody purification processes," *J. Chromatogr. B*, 878(9-10):798-806 (Mar. 2010).

McLean et al., "Purification of the therapeutic antibody trastuzumab from genetically modified plants using safflower Protein A-oleosin oilbody technology," *Transgenic Res.*, 21(6):1291-1301 (Dec. 2012).

Miller et al., "The rapid isolation of ribonuclease-free immunoglobulin G by protein A-sepharose affinity chromatography," *J. Immunol. Methods*, 24(1-2):111-125 (1978).

Tarrant et al., "Host cell protein adsorption characteristics during protein A chromatography," *Biotechnol. Prog.*, 28(4):1037-1044 (Jul. 2012).

Yigzaw et al., "Exploitation of the adsorptive properties of depth filters for host cell protein removal during monoclonal antibody purification," *Biotechnol. Prog.*, 22(1):288-296 (Jan./Feb. 2006).

Yoo et al., "Simultaneous removal of leached protein-A and aggregates from monoclonal antibody using hydrophobic interaction membrane chromatography," *J. Membr. Sci.*, 390-391:263-269 (Feb. 2012).

\* cited by examiner

REMOVAL OF IMPURITIES FROM PROTEIN A ELUATES

CROSS-REFERENCE TO RELATED PATENT APPLICATIONS

The present application claims benefit of priority to U.S. Provisional Application No. 61/923,380, filed Jan. 3, 2014, which is incorporated by reference for all purposes.

BACKGROUND OF THE INVENTION

Protein A is a 41 kD cell wall protein from *Staphylococcus aureas* that binds with a high affinity to the Fc region of antibodies. For example, Protein A binds with high affinity to human IgG1, IgG2 and IgG4 as well as to mouse IgG2a and IgG2b. Protein A binds with moderate affinity to human IgM, IgA and IgE as well as to mouse IgG3 and IgG1.

Protein G is an immunoglobulin-binding protein expressed in group C and G Streptococcal bacteria. Protein G binds to a broader range of IgG subclasses than protein A. Protein L was first isolated from the surface of bacterial species *Peptostreptococcus magnus* and also binds immunoglobulins via interaction with the kappa light chain.

Protein A/G is a recombinant fusion protein that combines IgG binding domains of both Protein A and Protein G. Protein A/G contains four Fc binding domains from Protein A and two from Protein G.

Each of the above-described proteins have been described for purifying immunoglobulins, with a Protein A being most commonly described in antibody purification. Very generally, Protein A, Protein G, Protein L, or Protein A/G are used in affinity chromatography to bind target antibodies from samples. The antibodies (bound to Protein A, G, L, or A/G) can then be separated from most other components of sample, and optionally further purified using other purification steps.

BRIEF SUMMARY OF THE INVENTION

In one embodiment, a polypeptide comprising a modified Protein G, Protein L, or Protein A/G that lacks antibody-binding activity is provided. In some embodiments, the modified Protein G, Protein L, or Protein A/G comprises one or more modified amino acids whose modification blocks antibody-binding activity. In some embodiments, the modified Protein G, Protein L, or Protein A/G comprises one or more modified lysine amino acids. In some embodiments, the modified lysine amino acids are acetylated lysines.

In some embodiments, the modified Protein G, Protein L, or Protein A/G comprises one or more Fc fragment-comprising proteins cross-linked at or near the binding sites on Protein G, Protein L, or Protein A/G, thereby sterically blocking antibody-binding activity.

In some embodiments, the modified Protein G, Protein L, or Protein A/G comprises one or more amino acid changes compared to an antibody-binding Protein G, Protein L, or Protein A/G, respectively, such that the polypeptide lacks antibody-binding activity but retains contaminant-binding activity.

In some embodiments, the modified Protein G, Protein L, or Protein A/G comprises sterically-blocked wildtype (or an antibody-binding variant of) Protein G, Protein L, or Protein A/G, respectively, such that the polypeptide lacks antibody-binding activity but retains contaminant-binding activity.

Also provided is a polypeptide comprising a modified Protein A that lacks antibody-binding activity, wherein the modified Protein A comprises one or more modified amino acids that block antibody-binding activity. In some embodiments, the modified Protein A comprises one or more modified lysine amino acids. In some embodiments, the modified lysine amino acids are acetylated lysines.

Also provided is a solid support or support matrix linked to a polypeptide comprising a modified Protein A, Protein G, Protein L, or Protein A/G that lacks antibody-binding activity between 0-30° C. In some embodiments, the modified Protein A, Protein G, Protein L, or Protein A/G comprises one or more modified amino acids that block antibody-binding activity. In some embodiments, the modified Protein A, Protein G, Protein L, or Protein A/G comprises one or more modified lysine amino acids. In some embodiments, the modified lysine amino acids are acetylated lysines.

In some embodiments, the modified Protein A, Protein G, Protein L, or Protein A/G comprises one or more Fc fragment-comprising proteins cross-linked to the Protein G, Protein L, or Protein A/G, thereby blocking antibody-binding activity.

In some embodiments, the modified Protein A, Protein G, Protein L, or Protein A/G comprises one or more amino acid changes compared to wildtype (or an antibody-binding variant of) Protein G, Protein L, or Protein A/G, respectively, such that the polypeptide lacks antibody-binding activity but retains contaminant-binding activity.

In some embodiments, the support matrix is a bead, membrane, or fiber.

Also provided are reaction mixtures comprising an antibody-comprising sample and (1) a modified Protein A, Protein G, Protein L, or Protein A/G that lacks antibody-binding activity, e.g., as described above or elsewhere herein or (2) a modified Protein A that lacks antibody-binding activity, wherein the modified Protein A comprises one or more modified amino acids that block antibody-binding activity.

Also provided are methods of purifying antibodies from sample comprising the antibodies and contaminants. In some embodiments, the method comprises contacting the sample with a polypeptide comprising a modified Protein A, Protein G, Protein L, or Protein A/G that lacks antibody-binding activity under conditions in which at least some contaminants bind to the polypeptide and the antibodies do not bind to the polypeptide; separating a solution comprising the antibodies from the contaminants bound to the polypeptide; contacting the solution comprising the antibodies to an antibody-binding Protein A, Protein G, Protein L, or Protein A/G under conditions to form a complex of the antibodies and the antibody-binding Protein A, Protein G, Protein L, or Protein A/G, thereby generating the complex and unbound components; separating the unbound components from the complex; and eluting the antibodies from the complex, thereby generating purified antibodies.

In some embodiments, the polypeptide is linked to a support matrix. In some embodiments, the support matrix is a bead, membrane, or fiber. In some embodiments, the modified Protein A, Protein G, Protein L, or Protein A/G comprises one or more modified amino acids that block antibody-binding activity. In some embodiments, the modified Protein A, Protein G, Protein L, or Protein A/G comprises one or more modified lysine amino acids. In some embodiments, the modified lysine amino acids are acetylated lysines.

In some embodiments, the modified Protein A, Protein G, Protein L, or Protein A/G comprises one or more Fc fragment-comprising proteins cross-linked to the Protein A, Protein G, Protein L, or Protein A/G, thereby blocking antibody-binding activity.

In some embodiments, the modified Protein A, Protein G, Protein L, or Protein A/G comprises one or more amino acid changes compared to an antibody-binding Protein A, Protein G, Protein L, or Protein A/G, respectively, such that the polypeptide lacks antibody-binding activity but retains contaminant-binding activity.

Also provided are methods of purifying antibodies from sample comprising the antibodies and contaminants, comprising, contacting the sample to an antibody-binding Protein A, Protein G, Protein L, or Protein A/G under conditions to form a complex of the antibodies and the active Protein A, Protein G, Protein L, or Protein A/G, thereby generating the complex and unbound components; separating the unbound components from the complex; eluting the antibodies from the complex, to form an eluate comprising the antibodies; contacting the eluate with a polypeptide comprising a modified Protein A, Protein G, Protein L, or Protein A/G that lacks antibody-binding activity under conditions in which at least some contaminants bind to the polypeptide and the antibodies do not bind to the polypeptide; and separating a solution comprising the antibodies from the contaminants bound to the polypeptide; thereby generating purified antibodies.

In some embodiments, the polypeptide is linked to a support matrix. In some embodiments, the support matrix is a bead, membrane, or fiber. In some embodiments, the modified Protein A, Protein G, Protein L, or Protein A/G comprises one or more modified amino acids that block antibody-binding activity. In some embodiments, the modified Protein A, Protein G, Protein L, or Protein A/G comprises one or more modified lysine amino acids. In some embodiments, the modified lysine amino acids are acetylated lysines.

In some embodiments, the modified Protein A, Protein G, Protein L, or Protein A/G comprises one or more Fc fragment-comprising proteins cross-linked to the Protein A, Protein G, Protein L, or Protein A/G, thereby blocking antibody-binding activity.

In some embodiments, the modified Protein A, Protein G, Protein L, or Protein A/G comprises one or more amino acid changes compared to wildtype or an antibody-binding variant of Protein A, Protein G, Protein L, or Protein A/G, respectively, such that the polypeptide lacks antibody-binding activity but retains contaminant-binding activity.

DETAILED DESCRIPTION OF THE INVENTION

I. Introduction

Provided are modified versions of proteins commonly used in antibody purification as well as kits and methods for their use. Specifically, modified Protein A, Protein G, Protein L, and Protein A/G are provided that lack antibody-binding activity. These polypeptides are useful in antibody purification in conjunction with native antibody-binding activity Protein A, Protein G, Protein L, and Protein A/G (i.e., having antibody binding activity) by removing contaminants that bind to native Protein A, Protein G, Protein L, and Protein A/G and thus end up as contaminants in antibody preparations.

Accordingly, in some embodiments, a method is provided of contacting an antibody sample with a modified Protein A, Protein G, Protein L, or Protein A/G in the course of purification, thereby removing contaminants that would have, or that have already, co-purified with the antibodies. Thus, in some embodiments, a protein sample is contacted with a native or an antibody-binding variant of Protein A, Protein G, Protein L, or Protein A/G under conditions to bind antibodies in the sample and allowing for purification of the antibodies from at least some other components of the sample. The resulting purified antibody mixture can nevertheless subsequently contain contaminants that also bound to the native or an antibody-binding variant of Protein A, Protein G, Protein L, or Protein A/G. These contaminants can be removed by subsequently (immediately after or after intervening purification steps) contacting the purified antibody mixture with a modified Protein A, Protein G, Protein L, or Protein A/G lacking antibody-binding activity. The contaminants that bound the native or an antibody-binding variant of Protein A, Protein G, Protein L, or Protein A/G will bind to the modified Protein A, Protein G, Protein L, or Protein A/G whereas the antibodies in the mixture will not. Thus, the antibodies can be separated from the bounds contaminants, resulting in a more pure antibody preparation.

Alternatively, in some embodiments, the modified Protein A, Protein G, Protein L, or Protein A/G can be contacted to a protein sample under conditions to allow any contaminants with affinity for native Protein A, Protein G, Protein L, or Protein A/G to bind to the modified Protein A, Protein G, Protein L, or Protein A/G, thereby removing such contaminants. The resulting protein mixture (reduced for Protein A, Protein G, Protein L, or Protein A/G-binding contaminants) can then be subsequently (immediately after or after intervening purification steps) contacted with native or an antibody-binding variant of Protein A, Protein G, Protein L, or Protein A/G, to bind and affinity purify the antibodies in the mixture, again resulting in a more pure antibody preparation compared to an equivalent purification scheme lacking the modified Protein A, Protein G, Protein L, or Protein A/G step.

The methods may be combined with other purification methods to achieve higher levels of purification. Examples include, but are not limited to, other methods commonly used for purification of antibodies, such as other forms of affinity chromatography, anion exchange chromatography, cation exchange chromatography, hydrophobic interaction chromatography, immobilized metal affinity chromatography, and additional mixed mode chromatography methods. Other options, include, but are not limited to precipitation, crystallization, and/or liquid partitioning methods.

II. Modified Protein A, G, L or A/G

Any type of modified Protein A, G, L, or A/G polypeptide that lacks antibody-binding activity can be used in the methods described herein. A modified Protein A, G, L, or A/G "polypeptide that lacks antibody-binding activity" refers to a modified Protein A, G, L, or A/G that has no more than 10% of a native antibody-binding (i.e., Fc domain-binding) polypeptide activity, e.g., the modified Protein A, G, L, or A/G has less than $1/10$, $1/100$, or $1/1000$ the binding activity of the native Protein A, G, L, or A/G. While it is appreciated that a "native" Protein A/G does not exist, for the purposes of this disclosure, "native Protein A/G" refers to a recombinant fusion protein that combines native IgG binding domains of both Protein A and Protein G. Protein A/G contains four Fc binding domains from Protein A and two from Protein G as known in the art.

Various variant forms of Protein A, G, L and A/G are known that bind antibodies. One such is MabSelect SuRe™, which is a native protein A with amino acid modifications designed to improve alkali stability. As used herein, "wild-type"; and "native" are used synonymously to mean a naturally-occurring protein.

Examples of modifications that reduce or eliminate antibody-binding activity of Protein A, G, L, or A/G include, but are not limited to, amino acid modification, amino acid mutation, and/or blocking of antibody-binding sites of Protein A, G, L, or A/G.

Modified Amino Acids

"Modified amino acids," as used herein, refers to chemical modification of naturally-encoded amino acids, resulting in reduction of antibody-binding to the modified protein. A variety of particular naturally-encoded amino acids, due to their particular chemical structure, are selectively reactive to specific chemicals, resulting in modification of the particular amino acid type without significant modification of other amino acids not of that type in the protein.

A number of examples of amino acid modification are known and can be applied to eliminate antibody-binding activity of Protein A, G, L, or A/G. For example, in one embodiment, lysine residues in the protein are modified by acetylation. This can be achieved, for example, by contacting the protein with a sufficient amount of acetic anhydride. In another embodiment, arginine residues in the protein are citrullinated (deaminated). In yet other embodiments, glutamine and asparagine are deamidated, converting the residues to glutamic acid and aspartic acid, respectfully. Yet other embodiments allow for eliminylation, i.e., the conversion to an alkene by beta-elimination of phosphothreonine and phosphoserine, or dehydration of threonine and serine. Other sorts of chemical modification of amino acids (e.g., as known in the art) in Protein A, G, L, or A/G can also be used.

Modified amino acids that inhibit the antibody-binding activity of Protein A, G, L, or A/G can also be formed in two or more steps. As an example, in one embodiment, one type of amino acid is converted to a second type of amino acid (e.g., arginine to lysine) which itself does not affect antibody-binding activity but then the second type of amino acid is modified (e.g., acetylated) to reduce antibody-binding activity of the protein.

Mutations

In other embodiments, one or more amino acid mutations are introduced into Protein A, G, L, or A/G to inhibit antibody-binding activity. In some embodiments, the resulting mutation protein is at least 90, 95, or 97% identical to the native or an antibody-binding variant of Protein A, G, L, or A/G. For example, in some embodiments, the modified protein comprises at least one but no more than 2, 3, 4, 5, 6, 7, 8, or 9 amino acid changes compared to native Protein A, G, L, or A/G. In some embodiments, the mutated Protein A, G, L, or A/G has temperature-sensitive antibody-binding activity. Examples of such proteins are described in, e.g., U.S. Patent Publication No. 2013/0317172. In other embodiments, the mutated Protein A, G, L, or A/G does not have antibody-binding activity at any temperature. For example, in some embodiments, the mutated Protein A, G, L, or A/G does not have antibody-binding activity between at least between 0-30° C.

A variety of Protein A mutations have been described that lack Fc-domain binding activity, albeit for other uses. See, e.g., U.S. Patent Publication No. 2013/0171183. For instance, in some embodiments, at least one of F5, Q9, Q10, S11, F13, Y14, L17, N28, I31, and/or K35 of the IgG Fc binding sub-domain of Protein A domain D is modified or substituted.

In addition to point mutations, one or more (e.g., 2, 3, 4, 5, 6, 7, 8, 9, 10 or more, e.g., 10-20, 10-30 amino acids) amino acid deletions or insertions can be made in Fc-binding regions of Protein A, G, L, or A/G, thereby blocking or eliminating antibody-binding activity.

Mutations can be introduced by random mutagenesis or by site-directed mutagenesis. Basic texts disclosing the general methods of mutagenesis and recombinant techniques include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Blocked Protein A

In yet another aspect, Protein A, G, L, or A/G can be treated with a blocking agent that blocks antibody-binding activity of Protein A, G, L, or A/G. For example, in some embodiments, Protein A, G, L, or A/G are contacted with a Fc-domain containing proteins (e.g., a full-length antibody tetramer or fragment thereof) and the resulting complex is cross-linked. Exemplary cross-linking agents include, but are not limited to, dimethyl suberimidate, the N-hydroxysuccinimide-ester crosslinker BS3, dicyclohexylcarbodiimide (which activates carboxyl groups to conjugate to primary amines), and formaldehyde. Cross-linking provides an advantage that the blocking agent will not disassociate from the Protein A, G, L, or A/G during the methods described herein for removal of contaminants. However, cross-linking is not necessary in scenarios in which the complex of Protein A, G, L, or A/G and blocking agent are used under conditions that do not significantly disassociate the complex.

Methods of Screening

As desired, further modified proteins with reduced antibody-binding activity can be screened for and selected. Thus, in some embodiments, Protein A, G, L, or A/G is contacted with a particular amino acid modifying agent and/or blocking agent, and/or mutations are introduced (e.g., recombinantly) into Protein A, G, L, or A/G and the resulting proteins are screened for antibody-binding activity. Antibody-binding activity can be assayed by, for example, 1) using an immunoassay (e.g., an ELISA); 2) measuring binding activity directly via surface plasmon resonance; 3) Static or dynamic light scattering; or other technique that measures protein-protein or antibody-protein binding. Proteins with reduced antibody-binding activity can then be selected. Using an ELISA, for example, reduced antibody binding would result in, e.g., a modified protein A that produced little or no signal from the ELISA assay (e.g., little or no fluorescence, visible light, radioactivity, etc., depending upon the reporter group).

III. Support Matrices

As noted above, in purifying target antibodies, it can be desirable to link either native or an antibody-binding variant of Protein A, G, L, or A/G and/or modified Protein A, G, L, or A/G lacking antibody-binding activity to a solid support. This allows, for example, for separation of components of a mixture that binds to the native or modified Protein A, G, L, or A/G from other components of the mixture. As described above, in the case of native or an antibody-binding variant of Protein A, G, L, or A/G, the components binding the Protein A, G, L, or A/G are generally desired antibodies whereas those components binding the modified Protein A, G, L, or A/G are non-antibody components that otherwise occur as contaminants in an antibody preparation.

A "solid support" refers to a material or group of materials having a rigid or semi-rigid surface or surfaces. In some embodiments, the solid support takes the form of thin films or membranes, beads, bottles, dishes, fibers, woven fibers, shaped polymers, particles, and microparticles, including but not limited to, microspheres. A solid support can be formed, for example, from an inert solid support, including but not limited to, natural material, such as glass and collagen, or synthetic material, such as acrylamide, cellulose, nitrocellulose, silicone rubber, polystyrene, polyethylene vinyl acetate, polypropylene, polymethacrylate, polyethylene, polysilicates, polyethylene oxide, polycarbonates, teflon, fluorocarbons, nylon, polyanhydrides, polyglycolic acid, polylactic acid, polyorthoesters, polypropylfumarate, glycosaminoglycans, and polyamino acids. Frequently, some functional groups, e.g., carboxylic acid (—COOH), free amine (—NH2), and sulfhydryl (—SH) groups, naturally present on the surface of a carrier can be used for peptide linkage. In case no such functional group is naturally available, a desired functional group, such as a carboxylic acid group, or a moiety known to be a partner of a binding interaction (such as avidin that is capable of binding biotin) may be attached to such solid support. In some embodiments, the solid support is a carboxylated latex or magnetic microsphere. Numerous methods are known in the art for linking proteins to a solid surface. As one example, a linking agent (including but not limited to N-hydroxisulfosuccinimide (NHSS) optionally with 1-Ethyl-3-[3-dimethylaminopropyl]carbodiimide hydrochloride (EDC)) can be used to link a protein to a solid support.

In some embodiments, the solid support is a support matrix. A variety of support matrices can be used. Generally, the support matrix will be a hydrophilic polymer that allows for linkage of the ligand, optionally via a spacer.

In some embodiments, the base matrix is hydrophilic and in the form of a polymer, e.g. a polymer that is insoluble and more or less swellable in water. Suitable polymers include, but are not limited to polyhydroxy polymers, e.g. based on polysaccharides, such as agarose, dextran, cellulose, starch, pullulan, etc. and completely synthetic polymers, such as polyacrylic amide, polymethacrylic amide, poly(hydroxyalkylvinyl ethers), poly(hydroxyalkylacrylates) and polymethacrylates (e.g. polyglycidylmethacrylate), polyvinyl alcohols and polymers based on styrenes and divinylbenzenes, and copolymers in which two or more of the monomers corresponding to the above-mentioned polymers are included. Polymers, which are soluble in water, may be derivatized to become insoluble, e.g. by cross-linking and by coupling to an insoluble body via adsorption or covalent binding. Hydrophilic groups can be introduced on hydrophobic polymers (e.g. on copolymers of monovinyl and divinylbenzenes) by polymerisation of monomers exhibiting groups which can be converted to OH, or by hydrophilization of the final polymer, e.g. by adsorption of suitable compounds, such as hydrophilic polymers. In some embodiments, the support is an UNOsphere™ support, a polymer produced from water-soluble hydrophilic monomers (Bio-Rad, Hercules, Calif.). Alternatively, the matrix is agarose (GE Sepharose or Sterogene Superflow and Ultraflow).

IV. Kits

In some embodiments, the modified Protein A, G, L, or A/G that lacks antibody-binding activity is packaged in a kit. In some embodiments, the kits further comprise other reagents, for example other reagents as described herein. For example, in some embodiments, the kit comprises at least one container comprising modified Protein A, G, L, or A/G and a second container comprising native or an antibody-binding variant of Protein A, G, L, or A/G. Instructions can optionally be provided in or with the kit.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of purifying antibodies from a sample comprising the antibodies and contaminants, the method comprising the steps in the following order:
    contacting the sample with a polypeptide comprising a modified Protein A, modified Protein G, modified Protein L, or modified Protein A/G that lacks antibody-binding activity under conditions in which at least some contaminants bind to the polypeptide and the antibodies do not bind to the polypeptide wherein said polypeptide has been recombinantly modified by changing one or more amino acid compared to an unmodified antibody-binding Protein A, an unmodified antibody-binding Protein G, an unmodified antibody-binding Protein L or an unmodified antibody-binding Protein A/Q, or chemically modified either by cross-linking one or more Fc fragment containing proteins to said polypeptide or by acetylation of one or more lysine residue so as to block antibody binding activity but retain contaminant binding activity of said polypeptide, and wherein said modified Protein A, said modified Protein G, said modified Protein L, or said modified Protein A/G does not have antibody-binding activity at any temperature,
    separating a solution comprising the antibodies from the contaminants bound to the polypeptide;
    contacting the solution comprising the antibodies to the unmodified antibody-binding Protein A, the unmodified antibody-binding Protein G, the unmodified antibody-binding Protein L, or the unmodified antibody-binding Protein A/G under conditions to form a complex of the antibodies with the unmodified antibody-binding Protein A, the unmodified antibody-binding Protein G, the unmodified antibody-binding L, or the unmodified antibody-binding Protein A/G, thereby generating the complex and unbound components;
    separating the unbound components from the complex; and eluting the antibodies from the complex, thereby generating the purified antibodies.

2. The method of claim 1, wherein the polypeptide is linked to a support matrix.

3. The method of claim 1, wherein the modified Protein A, modified Protein G, modified Protein L, or modified Protein A/G comprises one or more modified amino acids that block antibody-binding activity.

4. The method of claim 3, wherein the modified Protein A, modified Protein G, modified Protein L, or modified Protein A/G comprises one or more modified lysine amino acids.

5. The method of claim 4, wherein the modified lysine amino acids are acetylated.

6. The method of claim 1, wherein the modified Protein A, modified Protein G, modified Protein L, or modified Protein A/G comprises one or more Fc fragment-comprising proteins cross-linked to Protein A, Protein G, Protein L, or Protein A/G, thereby blocking antibody-binding activity.

7. The method of claim 1, wherein the modified Protein A, modified Protein G, modified Protein L, or modified Protein A/G comprises one or more amino acid changes compared to the unmodified antibody-binding Protein A, the unmodified antibody-binding Protein G, the unmodified antibody-binding Protein L, or the unmodified antibody-binding Protein A/G, respectively, such that the polypeptide lacks antibody-binding activity but retains contaminant-binding activity.

8. The method of claim 1, wherein the polypeptide comprises the modified Protein A which comprises at least one amino acid substitution at amino acid residue of F5, Q9, Q10, S11, F13, Y14, L17, N28, I131, and/or K35 in the IgG Fc binding sub-domain of Protein A domain D.

9. The method of claim 1, wherein the modified Protein A, modified Protein G, modified Protein L, or modified Protein A/G comprises one or more amino acid deletion or insertion in an Fc-binding region.

10. A method of purifying antibodies from a sample comprising the antibodies and contaminants, the method comprising the steps in the following order:
    contacting the sample to an unmodified antibody-binding Protein A, an unmodified antibody-binding Protein G, an unmodified antibody-binding Protein L, or an unmodified antibody-binding Protein A/G under conditions to form a complex of the antibodies and with the unmodified antibody-binding Protein A, the unmodified antibody-binding Protein G, the unmodified antibody-binding L, or the unmodified antibody-binding Protein A/G, thereby generating the complex and unbound components;
    separating the unbound components from the complex; and
    eluting the antibodies from the complex, to form an eluate comprising the antibodies;
    contacting the eluate with a polypeptide comprising a modified Protein A, modified Protein G, modified Protein L, or modified Protein A/G that lacks antibody-binding activity under conditions in which at least some contaminants bind to the polypeptide and the antibodies do not bind to the polypeptide, wherein said polypeptide has been recombinantly modified by changing one or more amino acid compared to the unmodified Protein A, the unmodified Protein G, the unmodified Protein L or the unmodified Protein A/G, or chemically modified either by cross-linking one or more Fc fragment containing proteins to said polypeptide or by acetylation of one or more lysine residue so as to block antibody binding activity but retain contaminant binding activity of said polypeptide, and wherein said modified Protein A, said modified Protein G, said modified Protein L, or said modified Protein A/G does not have antibody-binding activity at any temperature; and
    separating a solution comprising the antibodies from the contaminants bound to the polypeptide; thereby generating the purified antibodies.

11. The method of claim 10, wherein the polypeptide is linked to a support matrix.

12. The method of claim 10, wherein the modified Protein A, modified Protein G, modified Protein L, or modified Protein A/G comprises one or more modified amino acids that block antibody-binding activity.

13. The method of claim 12, wherein the modified Protein A, modified Protein G, modified Protein L, or modified Protein A/G comprises one or more modified lysine amino acids.

14. The method of claim 10, wherein the modified Protein A, modified Protein G, modified Protein L, or modified Protein A/G comprises one or more Fc fragment-comprising proteins cross-linked to Protein A, Protein G, Protein L, or Protein A/G, thereby blocking antibody-binding activity.

15. The method of claim 10, wherein the modified Protein A, the modified Protein G, the modified Protein L, or the modified Protein A/G comprises one or more amino acid changes compared to the unmodified antibody-binding Protein A, the unmodified antibody-binding Protein G, the unmodified antibody-binding Protein L, or the unmodified antibody-binding Protein A/G, respectively, such that the polypeptide lacks antibody-binding activity but retains contaminant-binding activity.

16. The method of claim 10, wherein the polypeptide comprises the modified Protein A which comprises at least one amino acid substitution at amino acid residue of F5, Q9, Q10, S11, F13, Y14, L17, N28, I131, and/or K35 in the IgG Fc binding sub-domain of Protein A domain D.

17. The method of claim 10, wherein the modified Protein A, modified Protein G, modified Protein L, or modified Protein A/G comprises one or more amino acid deletion or insertion in an Fc-binding region.

* * * * *